(12) United States Patent
Kolsky

(10) Patent No.: US 8,906,429 B1
(45) Date of Patent: Dec. 9, 2014

(54) MEDICAL CANNABIS LOZENGES AND COMPOSITIONS THEREOF

(71) Applicant: Jeffrey A. Kolsky, San Francisco, CA (US)

(72) Inventor: Jeffrey A. Kolsky, San Francisco, CA (US)

(*) Notice: Subject to any disclaimer, the term of this patent is extended or adjusted under 35 U.S.C. 154(b) by 0 days.

(21) Appl. No.: 14/103,788

(22) Filed: Dec. 11, 2013

(51) Int. Cl.
- *A01N 65/00* (2009.01)
- *A61K 31/352* (2006.01)
- *A61K 31/05* (2006.01)
- *A61K 36/185* (2006.01)

(52) U.S. Cl.
CPC .............. *A61K 36/185* (2013.01); *A61K 31/352* (2013.01); *A61K 31/05* (2013.01)
USPC ........................................................ 424/725

(58) Field of Classification Search
None
See application file for complete search history.

(56) References Cited

U.S. PATENT DOCUMENTS

2010/0222437 A1* 9/2010 Munoz Blanco et al. ..... 514/680

* cited by examiner

*Primary Examiner* — Michael Meller
(74) *Attorney, Agent, or Firm* — Ray K. Shahani, Esq.; Kin H. Lai

(57) ABSTRACT

A method for optimizing the therapeutic effects provided by CBD on the one hand, and the psychotropic effects provided by THC on the other hand, in a sublingual medicament, the method includes the steps of obtaining a concentrated extract of *cannabis* in which the concentration of CBD is known and the concentration of THC is known, formulating a hydrophilic mixture containing ingredients such as sugar, corn syrup, xylitol, purified water, organic flavorings, coconut oil, and concentrated extract of *cannabis*, wherein the amount of CBD is as high as possible and where the amount of THC is precisely controlled, forming lozenges, and administering the medicament.

9 Claims, 4 Drawing Sheets

Tetrahydrocannabinol THC

Cannabidiol CBD

MEDICAL CANNABIS LOZENGES AND COMPOSITIONS THEREOF

RELATED APPLICATIONS

None.

FIELD OF THE INVENTION

This invention relates to a variety of medical *cannabis* lozenges and hard candies, and more particularly, to lozenges and hard candies that contain different controlled levels of cannabidiol and tetrahydrocannabinol.

BACKGROUND OF THE INVENTION

A psychoactive drug, psychopharmaceutical, or psychotropic is a chemical substance that crosses the blood-brain barrier and acts primarily upon the central nervous system where it affects brain function, resulting in alterations in perception, mood, consciousness, cognition, and behavior.[1] These substances may be used recreationally, to purposefully alter one's consciousness, or as entheogens, for ritual, spiritual, and/or shamanic purposes, as a tool for studying or augmenting the mind. Many psychoactive drugs have therapeutic utility, e.g., as anesthetics, analgesics, or for the treatment of psychiatric disorders.

Psychoactive substances often bring about subjective changes in consciousness and mood that the user may find pleasant (e.g. euphoria) or advantageous (e.g. increased alertness) and are thus reinforcing. Thus, many psychoactive substances are abused, that is, used excessively, despite health risks or negative consequences. With sustained use of some substances, psychological and physical dependence ("addiction") may develop, making the cycle of abuse even more difficult to interrupt. Drug rehabilitation aims to break this cycle of dependency, through a combination of psychotherapy, support groups, maintenance and even other psychoactive substances. However, the reverse is also true in some cases, that certain experiences on drugs may be so unfriendly and uncomforting that the user may never want to try the substance again. This is especially true of the deliriants (e.g. Jimson weed) and powerful dissociatives (e.g. *Salvia divinorum*). Most purely psychedelic drugs are considered to be non-addictive (e.g. LSD, psilocybin, mescaline). "Psychedelic amphetamines" or empathogen-entactogens (such as MDA and MDMA) may produce an additional stimulant and/or euphoriant effect, and thus have an addiction potential.

Medical *cannabis* has several potential beneficial effects. Medical marijuana is helpful to people who experience chronic non-cancer pain, vomiting and nausea caused by chemotherapy. The drug can also help with treating symptoms of AIDS patients. As of 2today, the use of medical marijuana is legalized in over 20 U.S. states, and legalization of marijuana for any purpose by individuals over the age of 18 ha been approved in 2 different states. Animal studies show cannabinoids found in marijuana may have analgesic and anti-inflammatory effects, antitumor effects, and anticancer effects, including the treatment of breast and lung cancer.

Medical *cannabis* (or medical marijuana) refers to the use of *cannabis* and its constituent cannabinoids, such as Cannabidiol ("CBD"), as medical therapy to treat disease or alleviate symptoms. *Cannabis* has been used to reduce nausea and vomiting in chemotherapy and people with AIDS, and to treat pain and muscle spasticity.

Medical *cannabis* can be administered by a variety of routes, including vaporizing or smoking dried bud and leaf portions, eating leaf or extracts, and taking capsules. Synthetic cannabinoids are available as prescription drugs in some countries. Medical *cannabis* can also be made into an edible form such as lozenges, candies, baked goods.

Tetrahydrocannabinol THC, is the principal psychoactive constituent of the *cannabis* plant. An aromatic terpenoid, THC has a very low solubility in water, but good solubility in most organic solvents, specifically lipids and alcohols. In general, THC has mild to moderate analgesic effects, and *cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects. Evidence suggests that THC helps alleviate symptoms suffered both by AIDS patients, and by cancer patients undergoing chemotherapy, by increasing appetite and decreasing nausea. It has also been shown to assist some glaucoma patients by reducing pressure within the eye, and is used in the form of *cannabis* by a number of multiple sclerosis patients, who use it to alleviate neuropathic pain and spasticity.

Cannabidiol ("CBD") is one of at least 85 cannabinoids found in *cannabis*. It is a major constituent of the plant, second to THC, and represents up to 40% in its extracts. Compared with THC, CBD is not psychoactive in healthy individuals, and is considered to have a wider scope of medical applications than THC, including to epilepsy, multiple sclerosis spasms, anxiety disorders, bipolar disorder, schizophrenia, nausea, convulsion and inflammation, as well as inhibiting cancer cell growth.

*Cannabis* growers have been developing different strains of *cannabis* plants that have different THC and CBD levels. Medical *cannabis* users have been demanding medical *cannabis* products that have CBD as the main active ingredient, and little or no THC, providing some of the medicinal benefits of *cannabis* without the psychoactive effects caused mainly by THC.

U.S. Patent Publication No. 20020136752 by Whittle et al., dated Sep. 226, 2002, is directed to pharmaceutical formulations for use in the administration of medicaments, in particular lipophilic medicaments, via mucosal surfaces. Paragraph 27 states: "Both sublingual and buccal formulations depend on the efficient transfer of medicament from a hydrophilic vehicle to the mucous membrane of the sublingual or buccal mucosae. Transfer of medicament through the interstices between or through epithelial cells is governed principally by the lipid solubility of the medicament. Where a drug is water insoluble this is a further barrier to absorption from the sublingual area. There are therefore physical and biological limitations on the therapeutic usefulness of lipophilic medicaments such as, for example, *cannabis* and cannabinoids given by mouth and swallowed."

ADVANTAGES AND SUMMARY OF THE INVENTION

The present invention relates to medical *cannabis* lozenges that are made from concentrated *cannabis* oil. The medical *cannabis* lozenges of the present invention are both sublingual and digestive and have a high CBD level and a wide range of THC levels. Providing users an option to decide the level of acceptable psychoactive effects caused mainly by THC, while getting the medical benefits of CBD. Applicant submits there are no such products currently available.

The present invention relates to orally administered medical *cannabis* delivery product that has a high CBD content for medical purposes and a controlled level of THC.

One object and advantage of the present invention is to provide a more socially acceptable, easier and more convenient way for delivery of medical *cannabis*.

Another object and advantage of the present invention is to provide a more taste oriented option for edible medical *cannabis* products compared to oils or extracts.

Yet another object and advantage of the present invention is to provide a way to fully capitalize on the medical benefits of CBD in medical *cannabis* products.

Yet another object and advantage of the present invention is to eliminate or minimize the psychoactive effects of THC in medical *cannabis* products, or otherwise control the level of THC in a medicament.

Yet another object and advantage of the present invention is to allow users easily control the dosage of medical *cannabis* products by splitting the tablets.

Yet another object and advantage of the present invention is to provide a way for users to control the THC intake and its associated effects.

Yet another object and advantage of the present invention is to provide a way to select medical *cannabis* products made from *sativa* strains, *indica* strains or combination thereof.

Yet another object and advantage of the present invention is to provide a formulation and delivery method that overcomes physical and biological limitations on the therapeutic usefulness of lipophilic medicaments such as, for example, *cannabis* and cannabinoids given by mouth and swallowed.

Yet another object and advantage of the present invention is to provide sublingual and buccal formulations that depend on the efficient transfer of medicament from a hydrophilic vehicle to the mucous membrane of the sublingual or buccal mucosae.

Further details, objects and advantages of the present invention will become apparent through the following descriptions, and will be included and incorporated herein.

DETAILED DESCRIPTION OF THE PREFERRED EMBODIMENT

Figure 1:
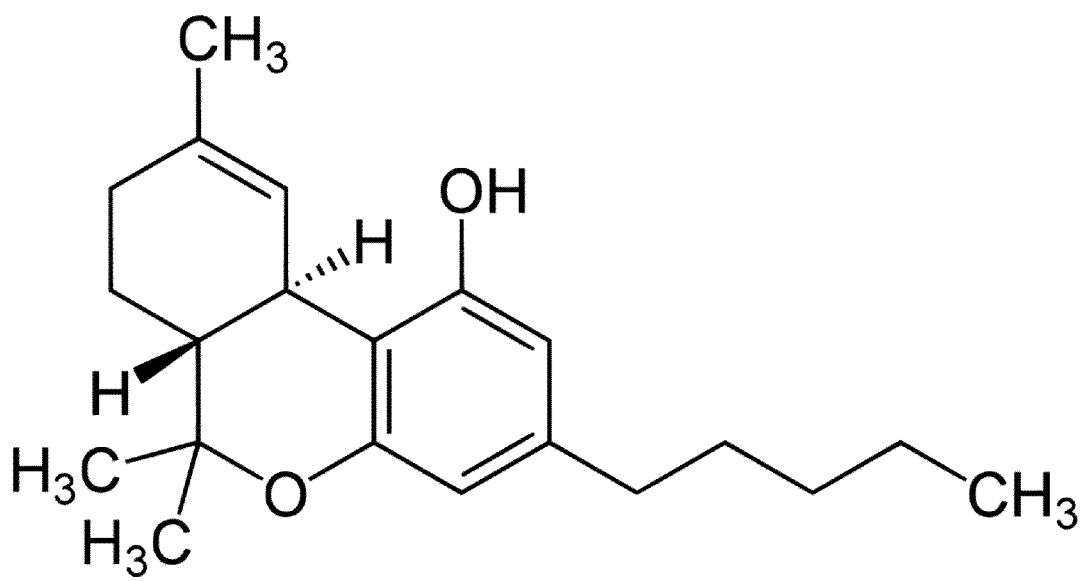
FIG. 1 is the chemical structure of Tetrahydrocannabinol ("THC").

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

Figure 3:
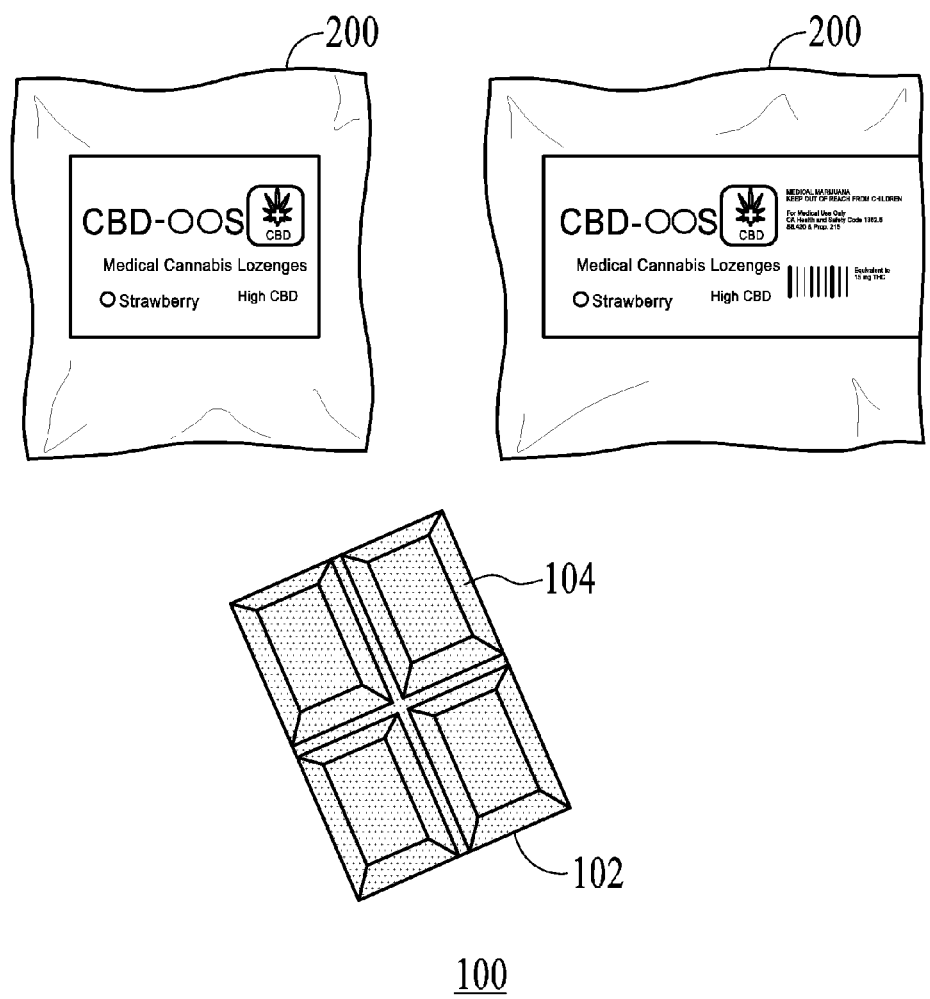
FIGS. 3 and 4 are representative views of samples 200 and 400 of medical *cannabis* lozenges 100 of the present invention.
Figure 4:
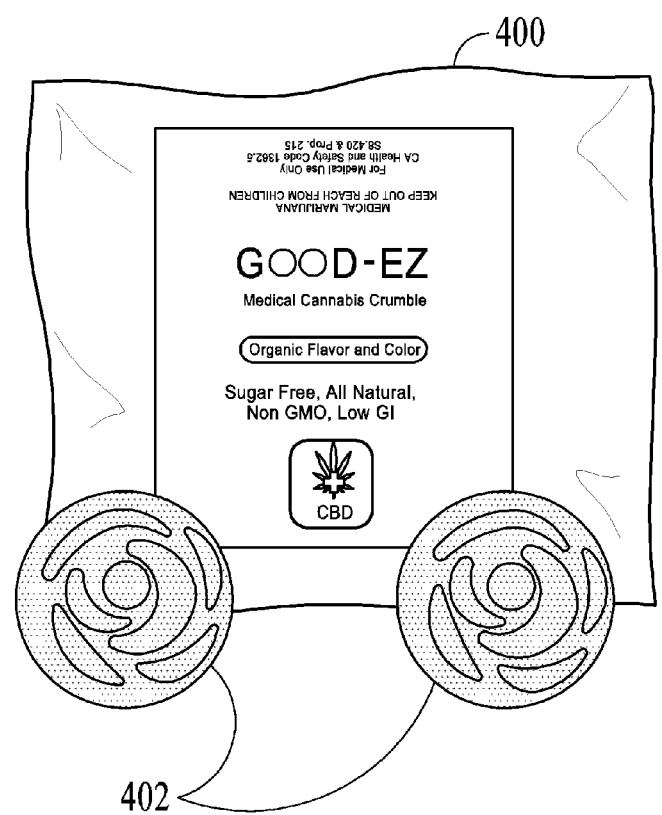

As best shown in FIG. 3, in one embodiment, medical *cannabis* lozenges 100 of the present invention take shape and form of conventional lozenge tablet or hard candy or crumble. In the lozenges format as best shown in FIG. 3, users can split individual tablet(s) 102 from the bar 104, according to the dosage desired. In alternative embodiments, medical *cannabis* lozenges 100' [not shown] can be made into a candy format such as an individual drop 402 as best shown in FIG. 4, a lollipop or even crumble. Regardless of formats, medical *cannabis* lozenges 100 are administered orally. Users can leave medical *cannabis* lozenges 100 in their mouth and let it dissolve naturally or ingest it, or combination thereof. Active ingredients of medical *cannabis* lozenges 100 are absorbed to users' body by sublingual administration and digestive tracts. Medical *cannabis* lozenges bar 104, as best shown in FIG. 3, are packaged in air-tight pouches 200 and distributed in compliance with U.S. National Food Safety standards.

Efficiency of delivery of active ingredients are enhanced by the size, shape, solubility and hardness of medical *cannabis* lozenges 100. In one embodiment, ideally medical *cannabis* lozenges tablets 102 should be made in regular lozenge size for ease of consumption.

Figure 2:
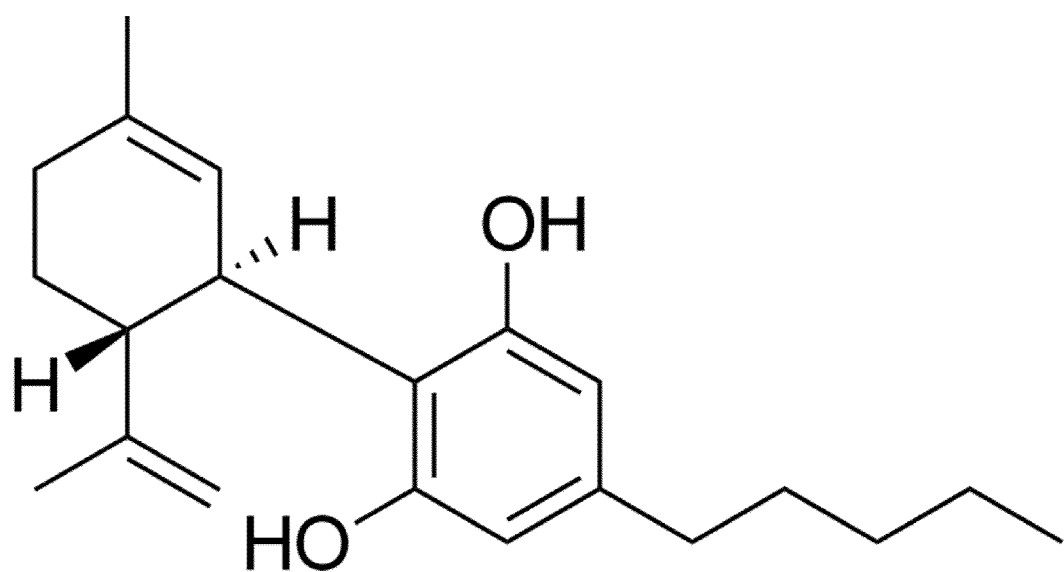
FIG. 2 is the chemical structure of Cannabidiol ("CBD").

In one embodiment, the most important active ingredient of medical *cannabis* lozenges 100 is Cannabidiol ("CBD"), and followed by Tetrahydrocannabinol ("THC"). CBD, chemical structure shown in FIG. 2, is a non psychoactive compound found in *cannabis* plants. While THC, chemical structure shown in FIG. 1, is the only psychoactive compound found in *cannabis* plants. CBD is not intoxicating and indeed it has been postulated that the presence of CBD in *cannabis* may alleviate some of the potentially unwanted side-effects of THC. The main focus of the present invention 100 is to capitalize on the medical applications of CBD by having a relatively high level, and a controlled level of THC according to users' preference of psychoactive effects of THC.

In one embodiment, THC delivery is not the main focus of medical *cannabis* lozenges 100 of the present invention. The purpose of medical *cannabis* lozenges 100 is to deliver the highest level of CBD possible and then allow users to determine how much THC is needed or desired to most effectively address their personal health needs.

In one embodiment, medical *cannabis* lozenges 100 have two active ingredients, viz., CBD and THC. The source of CBD and THC is the concentrated *cannabis* oil, which contribute solely to the CBD and THC content. In addition, a selective combination of the following inactive ingredients including cane sugar, syrup, filtered water, natural organic flavoring, Xylitol (all natural, U.S. manufactured from birch), coconut oil (raw, organic), natural organic colorings, which contribute to the volume/weight, shape, color, taste, texture, hardness and solubility of medical *cannabis* lozenges 100.

Concentrated *Cannabis* Oil:

Concentrated *cannabis* oil is apparently made from *cannabis* plants. Each *cannabis* strain has a particular Cannabinoids (including CBD and THC) profile. The concentrated *cannabis* oil used in the medical *cannabis* lozenges 100 of the present invention comes in two forms, viz. Base of food grade hexane and base of food grade ethanol. Depending on the combination of *cannabis* strains that the concentrated *cannabis* oil is made from, each batch of concentrated *cannabis* oil has a different CBD vs. THC ratio, which will be used for different variants of the present invention 100. Besides the CBD and THC content, concentrated *cannabis* oil used in the present invention 100 also takes into account the perceived psychoactive effects of the species of *cannabis* plants used, particularly *cannabis sativa* ("*sativa*") and *cannabis indica* ("*indica*") which are both annual herbaceous plants in the *Cannabis* genus. The perceived effects of *sativa* are well known for its cerebral high, hence used daytime as medical *cannabis*, while *indica* is perceived for its sedative effects which some prefer for night time use. Indica plants are normally shorter and stockier plants than *sativa* plants. They have wide, deeply serrated leaves and a compact and dense flower cluster. The effects of *indica* are predominantly physical and sedative. Due to the relaxing nature of *indica*, they are best used for non-active times of the day and before bed. A careful and skillful selection process of *cannabis* strains is conducted to ensure concentrated *cannabis* oil yielded has a particular CBD:THC ratio range and a desirable *sativa* and *indica* proportion.

Each batch of concentrated *cannabis* oil yielded will then be sent to a laboratory which its CBD and THC level will be tested using the liquid chromatography method. Liquid chromatography-mass spectrometry (LC-MS, or alternatively HPLC-MS) is an analytical chemistry technique that combines the physical separation capabilities of liquid chromatography (or HPLC) with the mass analysis capabilities of mass spectrometry (MS). Results of the LC-MS test will indicate CBD and THC content by weight in each batch of concentrated *cannabis* oil. Moreover each batch of concentrated *cannabis* oil will go through the phenol analysis to determine the phenol level. Since CBD and THC cannot be extracted individually from concentrated *cannabis* oil, sometimes mixing of various batches of concentrated *cannabis* oil is required to achieve a mixture that has the desirable CBD:THC ratio and *sativa* vs. *indica* proportion. However, in the future it is anticipated that separation of the CBD from the THC will also be possible, and then blending of THC and CBD to attain the optimum ration of CBD to THC can be achieved somewhat more efficiently but with the same result.

In one embodiment, medical *cannabis* lozenges 100 is to deliver at least three levels of CBD:THC ratios. In all three variants, the purpose is to achieve as a high CBD content as possible to gain the maximum medical benefits from CBD, and maintain a threshold which is a minimum of 25 mg per one unit of medical *cannabis* lozenges 100. Due to the fact that CBD cannot be extracted from the concentrated *cannabis* oil and added individually, there is a natural limit of how much CBD can be present in the present invention 100.

(One unit of medical *cannabis* lozenges 100 equals to 2 g to 4 g dry weight of *cannabis*, and the absolute weight of one unit is in the approximate range of 2 g to 15 g.)

1. The first variant, out of one unit of medical *cannabis* lozenges 100, it would have a maximum of 0-10 mg of THC and a minimum of 25 mg of CBD. Therefore, THC vs. CBD ratio by weight ranges from 0 to 0.40. The first variant is considered to have little to no psycho-activity. It is also believed with time and also been shown by some researches that small traces of THC although slightly psychoactive will be countered by the presence of high CBD content, especially in ratios of 1 mg THC to 7-10 mg or higher of CBD.

2. The second variant would be moderately psychoactive. Out of one unit of medical *cannabis* lozenges 100, a maximum of 10-40 mg of THC to a minimum of 25 mg of CBD. The THC vs. CBD ratio by weight in this variant ranges from 0 to 1.60. In this variant, a high *sativa* proportion concentrated *cannabis* oil is used. Hence, the psychoactive effects will be light and in many cases uplifting as the THC profile will be more reflective of the effects of the *sativa* variety of the *cannabis* plant. *Sativa* are generally viewed by medicine as being uplifting and anti depressant in nature, a day time use medicine.

3. The third variant would also be moderately psychoactive and has similar THC:CBD ratio of the second variant. Out of one unit of medical *cannabis* lozenges 100, a maximum of 10-40 mg of THC to a minimum of 25 mg of CBD. The THC vs. CBD ratio by weight in this variant also ranges from 0 to 1.60. The difference in the third variant is that a mix of *indica* and *sativa* proportion concentrated *cannabis* oil is used. These variant of medical *cannabis* lozenges 100 will be both moderately psychoactive mainly due to the elevated THC level (10-40 mg per one unit), while also offering increased medicinal relief from pain, inflamation, etc mainly from the high CBD level (25 mg+ per one unit). In this variant, there will be offerings of both *sativa* and *indica* which is more suitable for night time usage. *Sativa* as earlier described for use for treatment of depression, anxiety and low energy. Indica is more commonly used for pain, sleep issues and creating appetite. Although current researches indicate the THC compound is exactly the same in both *sativa* and *indica* strains, the difference in their perceived psychoactive and physiological effects distinguishes variant 2 and 3.

Manufacturing Process:

(Measurement based on making one unit of medical *cannabis* lozenges 100)

Firstly, the sole active ingredient concentrated *cannabis* oil with a particular THC:CBD ratio and *sativa* vs. *indica* proportion is selected. If the desirable THC:CBD ratio concentrated *cannabis* oil is not available, a few concentrated *cannabis* oils of different THC:CBD ratio is mixed to attain the desirable level. Concentrated *cannabis* oil or mixture will be weight to ensure that a minium of 25 mg CBD will be present in the final product. Secondly, inactive ingredients will be added to fill out the final weight and achieve a desirable non-medical properties such as taste, color, viscosity, hardness, etc. of medical *cannabis* lozenges 100. For example, sugar, corn syrup is added for taste and texture. Organic flavorings and colorings are added for taste and color. In some variants of medical *cannabis* lozenges 100, unpressed virgin organic coconut oil, non GMO Xylitol will be added for other purposes. The mixture will be heated and stirred until all ingredients are well mixed. It will then be poured into a mold and let set.

Sample Products:

As shown in FIG. 3, CBDOOS™ is one of the branded medical *cannabis* lozenges 200 available in the market now. It is made to achieve a gem or "see through" hard candy lozenge quality, appearance and texture. The formula for making 50 units consists of 2.25 cups of sugar, ⅔ cup of corn syrup, ¾ cup of purified water, 1 g of organic flavorings and lab determined proprietary amount of concentrated *cannabis* oil. In one embodiment, approximately 2.5 grams of *cannabis* oil will result in a product containing approximately 25 mg of CBDs per unit.

As shown in FIG. 4, GOOD-EZ™ is another branded medical *cannabis* lozenges 400 of the present invention available in the market now. It is made to be a sugar free xylitol based lozenge or crumble and are finished in a rose petal top 402, using 2.25 cups of USA sourced Birch non GMO Xylitol, ¼ cup of unpressed virgin organic coconut oil, 1 dram of organic flavorings and lab determined proprietary amount of concentrated *cannabis* oil. In one embodiment, approximately 2.5 grams of *cannabis* oil will result in a product containing approximately 25 mg of CBDs per unit.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

I claim:

1. A lozenge consisting essentially of hexane-extracted *cannabis sativa* oil, hexane-extracted *cannabis indica* oil, and xylitol.

2. The lozenge of claim 1 having a mass of between 2 grams and 15 grams.

3. The lozenge of claim 2 containing a minimum of 25 mg of CBD.

4. The lozenge of claim 2 containing a maximum of 40 mg of THC.

5. The lozenge of claim 1 further consisting essentially of an ingredient selected from the group consisting of sugar, corn syrup, flavorings, coloring agents, coconut oil, purified water and mixtures thereof.

6. A method for minimizing the psychoactive effects of THC in a human which is administered a sublingual lozenge, the method consisting essentially of:
   a) formulating the lozenge of claim 1; and
   b) administering the lozenge of claim 1 sublingually to a human until the lozenge is dissolved in the human.

7. The method of claim 6, wherein the step of formulating the lozenge is maximizing the CBD concentration.

8. The method of claim 6, wherein the step of formulating the lozenge is minimizing the THC concentration.

9. The method of claim 6, wherein the step of formulating the lozenge is maximizing the THC concentration.

* * * * *